United States Patent [19]

Morel

[11] Patent Number: 4,819,488

[45] Date of Patent: Apr. 11, 1989

[54] APPARATUS FOR TESTING THE RESISTANCE TO CLEAVAGE OF CARDBOARD TUBES

[75] Inventor: Jean-Michel Morel, Sens, France

[73] Assignee: Lhomme S.A., Pont sur Yonne, France

[21] Appl. No.: 162,318

[22] PCT Filed: May 29, 1987

[86] PCT No.: PCT/FR87/00188

§ 371 Date: Jan. 21, 1988

§ 102(e) Date: Jan. 21, 1988

[87] PCT Pub. No.: WO87/07379

PCT Pub. Date: Dec. 3, 1987

[30] Foreign Application Priority Data

May 29, 1986 [FR] France ............................ 86/07729

[51] Int. Cl.$^4$ ............................................. G01N 3/24
[52] U.S. Cl. ........................................ 73/845; 73/841
[58] Field of Search ............... 73/785, 788, 794, 796, 73/797, 799, 810, 817, 832, 834, 835, 845, 841, 856, 866, 865.9, 865.6

[56] References Cited

U.S. PATENT DOCUMENTS

| 2,650,493 | 9/1953 | Bowen, Jr. et al. ............. 73/794 |
| 2,657,573 | 11/1953 | Castricum ......................... 73/794 |
| 3,234,783 | 2/1966 | Hanson ............................. 73/797 |
| 3,797,304 | 3/1974 | Klinger ............................. 73/794 |
| 3,934,464 | 1/1976 | McCauley ......................... 73/832 |

FOREIGN PATENT DOCUMENTS

| 0530418 | 12/1940 | Fed. Rep. of Germany . |
| 3021482 | 12/1981 | Fed. Rep. of Germany . |
| 3320971 | 12/1983 | Fed. Rep. of Germany . |
| 0121586 | 7/1958 | U.S.S.R. ......................... 73/794 |
| 0868445 | 9/1981 | U.S.S.R. ......................... 73/794 |

Primary Examiner—Stewart J. Levy
Assistant Examiner—Robert R. Raevis
Attorney, Agent, or Firm—Sandler & Greenblum

[57] ABSTRACT

An apparatus for testing the resistance to cleavage of cardboard tubes which have previously been cut into test pieces which includes a key mandrel which is mounted free to rotate, at least one sleeve for each test piece having a different outer diameter, the inner diameter of at least one sleeve being approximately equal to the outer diameter of a test piece so that for each test piece there corresponds at least one sleeve intended to house the test piece. The key mandrel is adapted to receive each test piece surrounded by a corresponding sleeve. A drive device and belt are provided to rotatably drive an assembly which includes the key mandrel and a test piece housed in a corresponding sleeve.

10 Claims, 3 Drawing Sheets

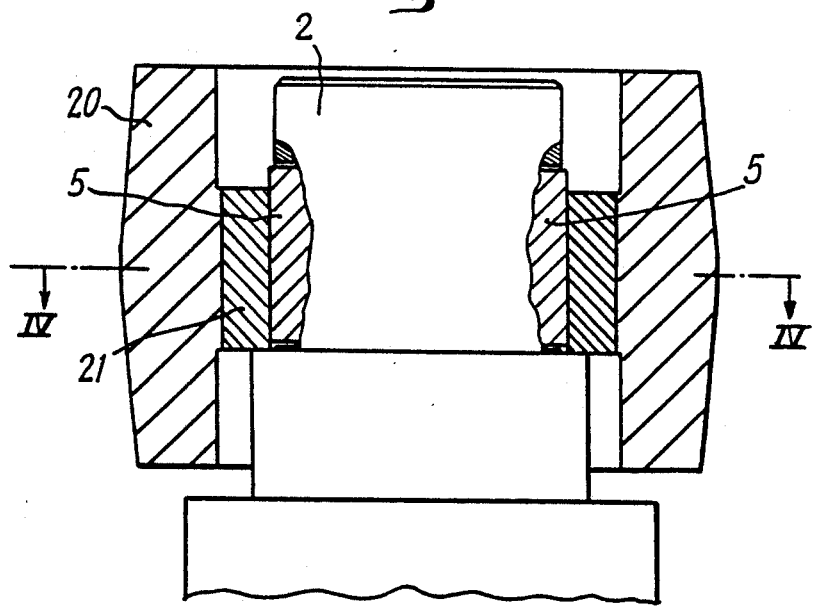
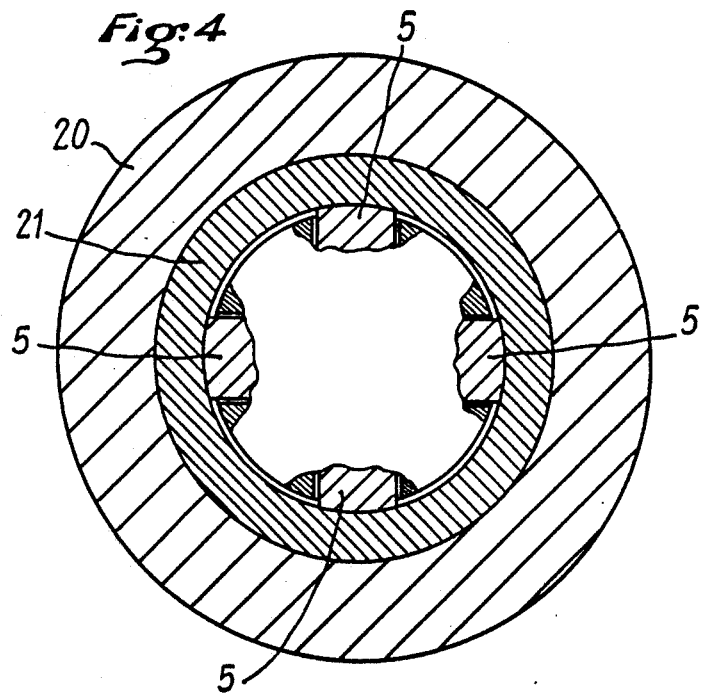

4,819,488

APPARATUS FOR TESTING THE RESISTANCE TO CLEAVAGE OF CARDBOARD TUBES

BACKGROUND OF THE INVENTION

1. Field of the Invention

The invention relates to an apparatus testing resistance to cleavage of cardboard tubes, in particular for tubes intended to be used as winding formers used, for example, in the printing industry.

2. Description of Background and Material Information

It is known to wind sheets of paper on mandrels comprised of cardboard tubes. Bobbins of this kind are handled by machines adapted to grasp from the inside the ends of tubes serving as winding formers.

Likewise, the bobbins, particularly in the printing industry, are positioned on unwinding machines or rotating machines in order to unwind the bobbins for printing the sheet of paper and/or cutting it and/or folding it, etc. To this end, machines used for holding the bobbins comprise two arms which are introduced into the two ends of the cardboard tube used as a winding former and which keys the latter by means of expansion heads provided with jaws capable of projecting towards the outside. The above-mentioned expansion heads are mounted free to rotate, so that the bobbin can freely turn as it unwinds.

It is clear that the winding formers are submitted to very heavy stress, caused by the weight of the bobbin, the speed and duration of its unwinding, to the pressure exerted by the expansion heads and, sometimes, to the braking stresses of the expansion heads which are blocked in rotation, in case, for example, of an emergency stop when the bobbin has a high kinetic energy.

The features of the cardboard tubes selected to be used as a winding former are therefore important and, up to now, the material used, the thickness of the tubes and other manufacturing parameters are chosen in an empirical manner with as the only resistance test, the actual operating test, by starting with the empirical observation that a tube resisting beyond a given time, as a function of the weight of the bobbin, should resist the entire time it is used.

It has been observed that cardboard tubes being used as winding formers are destroyed by cleavage or unflattening of the material at the end of a length of time which is a function of the above-mentioned stresses and more particularly a function of the weight of the bobbin. One can in effect observe that as the bobbin rotates (generally very quickly), each section of the mandrel, which turns with said bobbin, is alternately submitted to very different forces, the crushing caused by the weight occurring only when said section is turned upward.

There are already machines for testing the resistance of tubes to compression, to bending, to hardness (by ballbearings for example). These tests are used but are very inadequate when it is a matter of determining the features of a tube intended to be used, in particular, as a winding former.

This is why the inventor imagined an apparatus intended to test the resistance to the cleavage of cardboard tubes which are, to this end, cut in the form of samples or test pieces.

SUMMARY OF THE INVENTION

The machine according to the invention is remarkable in that it comprises a keying mandrel which is mounted free to rotate, at least one sleeve for each different outer diameter of the test pieces and whose inner diameter is close and at least equal to said outer diameter of the test pieces, so that for each test piece, there is at least one corresponding sleeve intended to house said test piece, the keying mandrel being adapted to receive, while keying it, each test piece surrounded by a corresponding sleeve, while a drive belt is provided in order to be stretched between said sleeve and a drive device, in order to rotatingly drive the assembly comprised of the keying mandrel, a test piece and a sleeve.

The machine according to the invention reconstitutes the stresses to which are submitted, in particular, the winding formers, the sleeves materially representing the bobbins whose weight is simulated by the tension of the drive belt.

Preferably, the inner diameter of a sleeve is very slightly higher than the outer diameter of the corresponding test pieces.

Generally, this play will always be the same whatever the inner diameter of the test piece to be tested and will be, for example, approximately 2/10 mm, which does not prevent forcibly introducing test pieces into said sleeves.

Preferably, several sleeves are provided whose outer diameters are all identical whatever their inner diameters may be.

In this manner, it is possible to test several test pieces having different outer diameters, while the driving speed will be able to be constant, given the constant outer diameter of the sleeves.

According to one embodiment, the keying mandrel is a mandrel having jaws expandible toward the outside in order to key under a certain pressure each test piece to be tested.

Preferably in this case, the keying mandrel is provided with an adjustment means and a measuring means of the pressure exerted by its jaws on the test pieces.

In order to simulate different bobbin weights, the drive belt can be provided with an adjustable tension means.

Preferably, the keying mandrel is provided with a brake device and the drive device of the drive belt of a clutch system, while an inertia wheel acting on said drive belt is provided, in order to test the resistance of the test pieces at braking.

According to one preferred embodiment, the drive device comprises a motor provided with a drive shaft connected by a transmission belt to a transmission pulley which is mounted free to rotate but which is affixed in rotation to a drive pulley, itself in gear with the drive belt.

Preferably, then, the transmission pulleys and drive pulleys are keyed onto a common axis of rotation, the latter and the axis of the keying mandrel being parallel and positioned in a substantially horizontal plane, while the shaft of the drive motor is substantially positioned at the plumb of the axis of rotation of the pulleys.

Also preferably, the motor is fastened onto a support plate mounted pivoting on a frame, while the axis of rotation of the transmission and drive pulleys is mounted in bearings which are fastened onto said support plate, which is connected in a journalled manner to a jack, intended to act on said plate and therefore on the axis of rotation, so as to adjust the tension of the drive belt, by modifying the axis included between said axis of rotation and the axis of the keying mandrel.

BRIEF DESCRIPTION OF THE DRAWINGS

The invention will be well understood by reading the following description and by referring to the attached drawings, in which:

FIG. 3 is an enlarged view, partially in cross section, of the end of the keying mandrel supporting a test piece and a sleeve, FIG. 4 is a cross section according to IV—IV of FIG. 3.

DETAILED DESCRIPTION OF THE INVENTION

Figure 1:
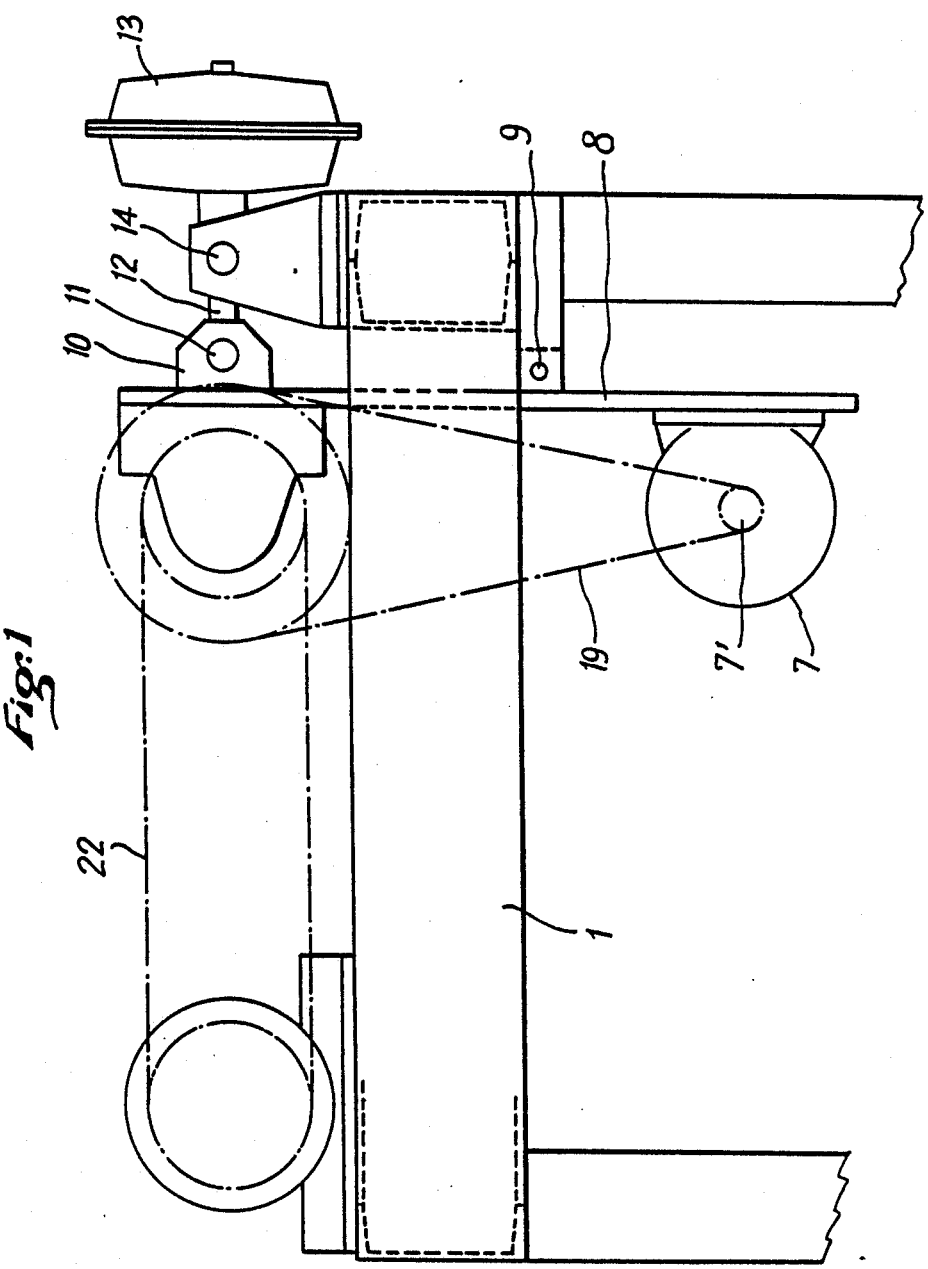
FIG. 1 is a schematic elevational view of a device according to the invention.
Figure 2:
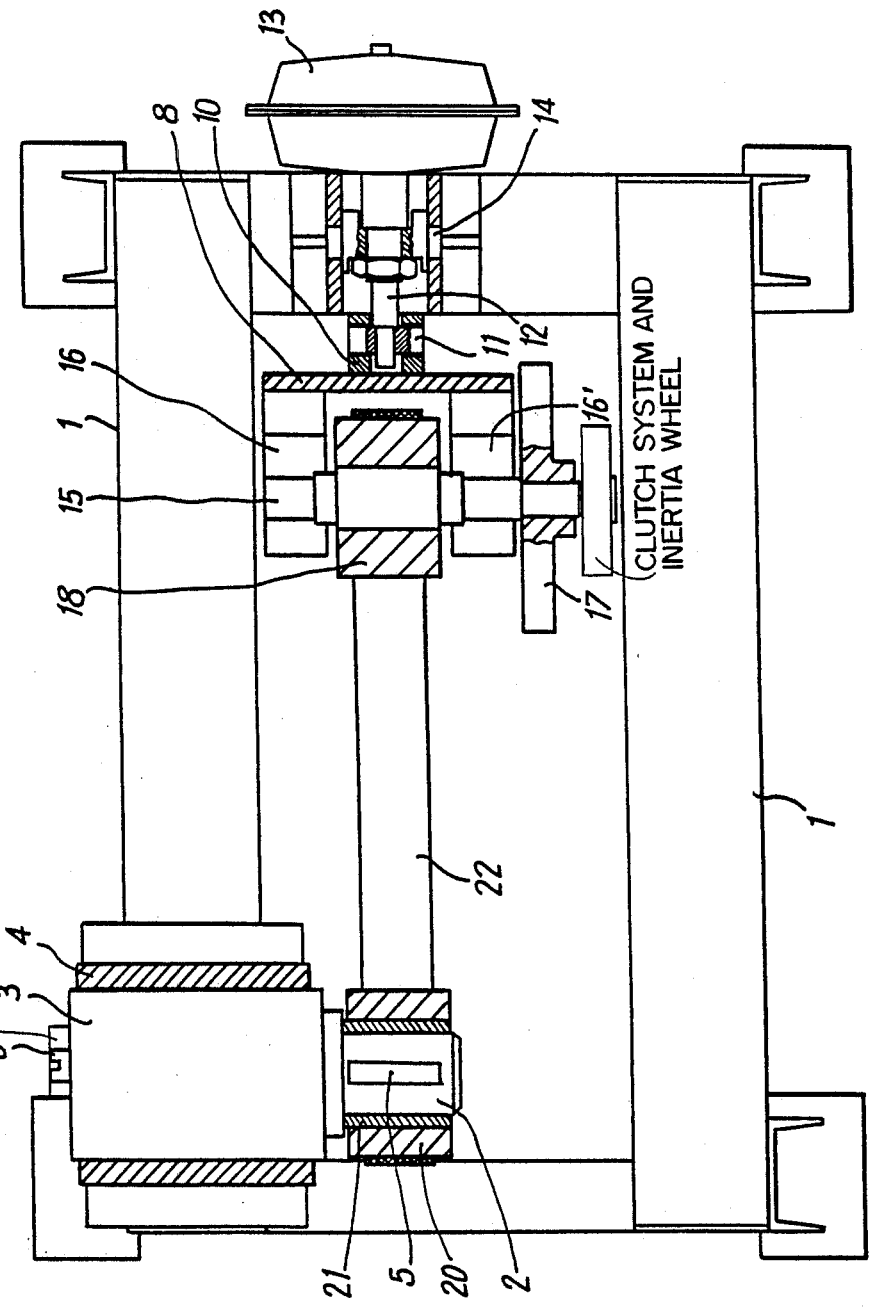
FIG. 2 is a plane view from above of FIG. 1, partially in cross section.

The machine according to the invention is fastened onto frame 1 (FIGS. 1 and 2) and comprises a mandrel 2 (FIGS. 2-4) one of whose ends is mounted free to rotate in a bearing 3, fastened onto frame 1 by means of a ring-shaped support 4 (FIG. 2).

Mandrel 2 is provided, at its free end, with jaws 5 (FIGS. 2-4) expandable toward the outside by any known means, fitted into bearing 3, and maneuverable, for example, by a nut or a screw 6 (FIG. 2) which allows furthermore for an adjustment of the locking pressure of jaws 5, as will be specified below.

A drive motor 7 provided with an outlet rotating shaft 7' (FIG. 1) is fastened onto a support plate 8, substantially vertical which is journalled, on the one hand, in a pivoting manner 9 to frame 1 (FIG. 1) and, on the other hand, by means of a stirrup 10 and an axis 11 to the stem 12 of a pneumatic jack 13 (FIGS. 1 and 2). The cylinder of jack 13 is further journalled in a pivoting manner around an axis 14 of the frame (FIGS. 1 and 2).

Substantially at the plumb and above motor shaft 7', is fitted an axis 15 mounted free to rotate in bearings 16 and 16' affixed to support plate 8 (FIG. 2). Axis 15 is parallel to shaft 7' and to the geometric axis of mandrel 2 with which it defines a substantially horizontal plane, while on said axis 15, are keyed two pulleys 17 and 18 (FIG. 2).

Between motor shaft 7' and pulley 17, is stretched a transmission strap 19 (FIG. 1).

In order to test cardboard tubes, slices are cut which are intended to be used as samples or test pieces.

The invention provides for positioning a plurality of sleeves such as 20 in FIGS. 2, 3 and 4.

All the sleeves can preferably present the same outer diameter and various inner diameters, as a function of the test pieces to be tested, as will be explained below.

Generally, the inner diameter of the test pieces, when it is a matter of testing winding formers, is standard, so that their outer diameters will be different solely because of the different thicknesses of the test pieces, but it is obvious that the outer diameter of the test pieces can be any diameter.

Each test piece 21 (FIGS. 2, 3 and 4) to be tested is introduced into a corresponding sleeve 20, i.e. having an inner diameter at least equal to the outer diameter of said test piece. The inventor however has found it preferable to provide a higher side of approximately 2/10 mm. for the inner diameter of the sleeve, in its portion intended to be in contact with the test piece, with respect to the outer diameter of said test piece (this play being preferably the same for all test pieces and corresponding sleeves). In FIG. 2, the length of test piece 21 is identical to the length of sleeve 20. Nevertheless, as an example, FIG. 3 shows a test piece which is slightly shorter than its sleeve, which makes it possible in particular to possibly provide (as FIG. 3 shows) a more significant play between the diameters on the sleeve openings, by thus facilitating the attachment of the test piece.

When test piece 21 is housed in its sleeve, the assembly is positioned on mandrel 2 (FIGS. 2, 3 and 4), and one acts on the adjustment screw 6 so as to ensure the expansion of the jaws which then exert a certain pressure on the inner wall of the test piece.

A transmission belt 22 (FIGS. 1 and 2) is then stretched between sleeve 20 and pulley 18.

The pneumatic jack 13 makes it possible to adjust the tension of belt 22 by more or less rotating support 8 which pivots in 9 on frame 1, which modifies the axis between the geometric axis of mandrel 2 and axis 15 of pulleys 17 and 18.

Motor 7, by means of its shaft 7', of transmission belt 19 and pulley 17, makes it possible to drive in rotation pulley 18 (affixed to axis 15) and thus belt 22. Belt 22 then drives in rotation the assembly comprised of mandrel 2, test piece 21 and sleeve 20.

Sleeve 20 materially represents a bobbin whose weight is determined by the adjustable tension of belt 22.

A significant number of test forms may then be effected.

It is in effect possible to vary and adjust, the pressure exerted by jaws 5 (screw 6), the tension of belt 22 (jack 13) and also of course the drive speed of said belt, by using a motor 7 at variable speed or pulleys of various diameters for strap 19 and which are intended to be keyed onto shaft 7' (position in height of motor 7 on plate 8 then being possibly adjustable).

It is for example possible to measure the lifetime (until the destruction by cleavage or unflattening) of a test piece under constant tension of belt 22, or to determine a breaking value by varying the tension of belt 22 as a function of time.

Other means are further provided, such as a brake device for mandrel 2 in order to study the behavior of the test tube in case of sudden braking (emergency stop for example). In this case, motor 7 is then provided with a clutch device and axis 15 is provided with an inertia wheel so as to perform resistance tests of the test pieces at braking after motor 7 has been disengaged the inertia wheel simulating the inertia of a rotating bobbin. Nevertheless, it is possible that pulley 17 may be conveniently chosen so as to act as an inertia wheel.

In the embodiment shown, the tension of belt 22 is in fact a function of the pneumatic pressure of jack 13, but an end adjustment of the tension of the belt is likewise provided by means, for example, of a return gear positioned on belt 22 and which would be combined with a dynamometer.

The invention which more particularly relates to tests for determining the nature of cardboard tubes to be selected for comprising winding formers, is not limited to this application, but may also be applied to tests of tubes submitted to stresses close or similar to those of winding formers.

Finally, many variations can clearly be imagined. The horizontal positioning of belt 22 is not mandatory, jack 13 may be hydraulic or replaced by any other mechanical means, likewise adjusting screw 6 can also be replaced by another means.

I claim:

1. Apparatus for testing the resistance to cleavage of cardboard tubes which have been previously cut into test pieces which comprises a keying mandrel which is mounted free to rotate, at least one sleeve for each test piece having a different outer diameter, the inner diameter of said at least one sleeve being approximately equal to the outer diameter of a test piece such that for each test piece there corresponds at least one sleeve for housing the test piece, the keying mandrel being adapted to receive each test piece which is housed in a corresponding sleeve, while a drive device and belt are provided to rotate a drive assembly that includes the keying mandrel and a test piece which is housed in an a corresponding sleeve, whereby the apparatus tests the resistance to cleavage of the cardboard tubes.

2. Apparatus according to claim 1, wherein the inner diameter of each sleeve is slightly larger than the outer diameter of a corresponding test piece.

3. Apparatus according to claim 1 wherein several sleeves are provided whose outer diameters are all identical.

4. Apparatus according to claim 1 wherein the keying mandrel is a mandrel having jaws which are outwardly expandable so as to key under a certain pressure.

5. Apparatus according to claim 4 wherein the keying mandrel is provided with an adjusting means and a means for measuring the pressure exerted by said jaws on the test pieces.

6. Apparatus according to claim 1 wherein said drive belt is provided with an adjustable tension means.

7. Apparatus according to claim 1 wherein the keying mandrel is provided with a brake and said drive device includes a clutch system and an inertia wheel that act on the drive belt so as to test the resistance of the test pieces during braking.

8. Apparatus according to claim 1 wherein the drive device includes a motor provided with a drive shaft connected by a transmission strap to a transmission pulley which is mounted free to rotate but which is affixed in rotation to a drive pulley which is connected to the drive belt.

9. Apparatus according to claim 8 wherein the transmission pulley and drive pulley are connected along a common axis of rotation which is parallel to the axis of rotation of the keying mandrel, and the said drive shaft of said motor is positioned substantially at the plum of the axis of rotation of the transmission and drive pulleys.

10. Apparatus according to claim 9 wherein the motor is fastened onto a support plate mounted which is pivotally mounted on a frame, and the axis of rotation of said transmission and drive pulleys are mounted in bearings which are fastened onto said support plate, the support plate is connected in a journalled manner to a jack that controls pivoting of the support plate thereby allowing for tensioning of the drive belt.

* * * * *